(12) United States Patent
Mehra et al.

(10) Patent No.: US 8,377,643 B2
(45) Date of Patent: Feb. 19, 2013

(54) SPLIT FLOW DEVICE FOR ANALYSES OF SPECIFIC-BINDING PARTNERS

(75) Inventors: Rajesh Mehra, Sunnyvale, CA (US); Kenneth P. Aron, Burlingame, CA (US); Madeline Netto, Fremont, CA (US)

(73) Assignee: Abaxis, Inc., Union City, CA (US)

( * ) Notice: Subject to any disclaimer, the term of this patent is extended or adjusted under 35 U.S.C. 154(b) by 188 days.

(21) Appl. No.: 12/721,784

(22) Filed: Mar. 11, 2010

(65) Prior Publication Data

US 2010/0233708 A1 Sep. 16, 2010

Related U.S. Application Data

(60) Provisional application No. 61/160,665, filed on Mar. 16, 2009.

(51) Int. Cl.
*G01N 33/53* (2006.01)
*C12N 11/16* (2006.01)
*C12M 1/00* (2006.01)

(52) U.S. Cl. ... 435/7.1; 435/174; 435/283.1; 435/287.1; 435/287.8; 436/501

(58) Field of Classification Search .......................... None
See application file for complete search history.

(56) References Cited

U.S. PATENT DOCUMENTS

| | | |
|---|---|---|
| 4,313,734 A | 2/1982 | Leuvering |
| 5,102,788 A | 4/1992 | Cole |
| 5,141,850 A | 8/1992 | Cole et al. |
| 5,160,701 A | 11/1992 | Brown et al. |
| 5,275,785 A * | 1/1994 | May et al. ..................... 422/408 |
| 5,415,994 A | 5/1995 | Imrich et al. |
| 5,451,504 A | 9/1995 | Fitzpatrick et al. |
| 5,559,041 A | 9/1996 | Kang et al. |
| 6,074,869 A * | 6/2000 | Pall et al. ................... 435/286.5 |
| 6,264,892 B1 | 7/2001 | Kaltenbach et al. |
| 7,294,503 B2 | 11/2007 | Quake et al. |
| 7,344,893 B2 | 3/2008 | Kirkegaard et al. |
| 2004/0214253 A1* | 10/2004 | Paek et al. ................... 435/7.92 |
| 2006/0078986 A1* | 4/2006 | Ly et al. ..................... 435/287.2 |
| 2007/0077170 A1 | 4/2007 | Tanaami et al. |
| 2011/0053289 A1* | 3/2011 | Lowe et al. ................... 436/501 |

FOREIGN PATENT DOCUMENTS

| | | |
|---|---|---|
| EP | 0 284 232 A1 | 9/1988 |
| EP | 0 505 636 A1 | 8/1991 |
| WO | WO 88/08534 A1 | 11/1988 |
| WO | WO 91/12336 | 8/1991 |

OTHER PUBLICATIONS

Stratagene Catalog, 1989, p. 39.*
Woong, "International Search Report," 4 pages, International Patent Appl. No. PCT/US2010/026948, Korean Intellectual Property Office (mailed Nov. 26, 2010).

(Continued)

*Primary Examiner* — Betty Forman
(74) *Attorney, Agent, or Firm* — Cooley LLP

(57) ABSTRACT

The present invention provides an analyte detection system for detecting a target analyte in a sample. In particular, the invention provides a detection system capable of one-step amplification of the detection signal by incorporating a secondary flow path that can deliver reagents to a reaction zone. Methods of using the detection system to detect analytes in samples, particularly biological samples, and kits comprising the detection system are also disclosed.

33 Claims, 4 Drawing Sheets

OTHER PUBLICATIONS

Woong, "Written Opinion of the International Searching Authority," 3 pages, International Patent Appl. No. PCT/US2010/026948, Korean Intellectual Property Office (mailed Nov. 26, 2010).

Chan CP et al., "New trends in immunoassays," Adv Biochem Eng Biotechnol., vol. 109:123-54, 2008.

Laderman El et al., "Rapid, sensitive, and specific lateral-flow immunochromatographic point-of-care device for detection of herpes simplex virus type 2-specific immunoglobulin G antibodies in serum and whole blood," Clin Vaccine Immunol., vol. 15(1):159-63, 2008.

Gupta S et al., "Characterization and optimization of gold nanoparticle-based silver-enhanced immunoassays," Anal Chem., vol. 79(10):3810-20, 2007.

Nitin N. et al., "Oligonucleotide-coated metallic nanoparticles as a flexible platform for molecular imaging agents," Bioconjug Chem., vol. 18(6):2090-6, 2007.

Bui MP et al., "Gold nanoparticle aggregation-based highly sensitive DNA detection using atomic force microscopy," Anal Bioanal Chem., vol. 388:5-6, 2007.

* cited by examiner

SPLIT FLOW DEVICE FOR ANALYSES OF SPECIFIC-BINDING PARTNERS

CROSS-REFERENCE TO RELATED APPLICATIONS

This application claims the benefit of U.S. Provisional Application No. 61/160,665, filed Mar. 16, 2009, which is herein incorporated by reference in its entirety.

FIELD OF THE INVENTION

The present invention relates to an analyte detection system for detecting a target analyte in a sample, e.g. a biological sample. In particular, the present invention provides a one-step detection system that allows for amplification of the detection signal by employing a secondary flow path that sequentially delivers reagents to a reaction zone.

BACKGROUND OF THE INVENTION

One of the most common types of assays used as a rapid point of care test to detect a particular analyte in a biological sample is a lateral flow strip-based assay. Such assays typically contain a binding partner for the analyte of interest coupled to a detectable label (i.e. labeled conjugates) and a porous membrane on which a capture protein (e.g. antibody or antigen) capable of binding the analyte of interest is immobilized. Labeled conjugates that are commonly used in these types of assays are antibodies or antigens coupled to gold nanoparticles or colored latex particles. An analyte present in the sample will bind to the labeled conjugate to form a complex. The complex continues to migrate through the porous membrane to the region where the capture protein is immobilized at which point the complex of analyte and labeled conjugate will bind to the capture protein. The presence of the analyte is then determined by detecting the labeled conjugate in the capture region of the porous membrane (e.g. by a color change of the capture line).

Although lateral flow strip-based assays have proven useful for rapid detection of some analytes in the clinical setting, such assays are inherently limited by their sensitivity due to the occurrence of a single binding event. Amplification of signals can be achieved, for example, by employing an enzyme as the detectable label. Lateral flow assays that employ enzyme label conjugates have been developed. However, these assays require multiple steps to wash the enzyme label conjugate from the capture region and to subsequently deliver the enzyme substrate. Amplification can also be effected in assays that employ nanoparticles as the detection label by intensifying the signal with silver particles (e.g. application of silver nitrate) or by deposition of reaction products from alkaline phosphatase, peroxidase, or β-galactosidase reactions. Similar to amplification in assays using enzyme label conjugates, amplification in nanoparticle-based assays also requires several steps to wash the unreacted conjugate from the capture region and apply the intensification solution.

Thus, there is a need in the art to develop one-step, e.g. rapid lateral flow assays with built-in amplification to provide sensitivity for the detection of analytes in samples, particularly biological samples.

SUMMARY OF THE INVENTION

The present invention is based in part on the discovery that the flow path of a sample in a lateral flow assay device can be split into two independent flow paths that flow parallel to one another in separate planes. By manipulating the fluidics of each of the flow paths separately, the second flow path may be used to deliver reagents, e.g. enzyme substrates or amplification reagents, to the capture region of the device after the analyte-conjugate complex has been captured by the immobilized binding partner and unbound conjugate has cleared from the capture region and absorbed into the absorbent pad. Accordingly, the present invention provides an analyte detection system that allows for the detection of a variety of analytes in a sensitive, one-step format.

In one embodiment, the present invention provides an analyte detection system comprising a first flow path and a second flow path, wherein the first flow path includes a sample loading region, a conjugate region and a capture region, wherein the second flow path includes a sample entry region, a substrate region and a substrate entry region, wherein the first flow path and the second flow path are in different planes and connected through the sample entry region, and wherein the substrate entry region is in fluid communication with the first flow path. In another embodiment, the substrate entry region comprises a semi-permeable membrane. In another embodiment, the first flow path further comprises an absorbent region downstream of the capture region.

In some embodiments, the first and second flow paths can be separated by a barrier layer. In one embodiment, the first flow path provides a faster flow through than the second flow path. The first and second flow paths can comprise a porous material. In another embodiment, the first flow path can comprise a porous material of higher porosity than the porous material found in the second flow path.

In further embodiments of the invention, the conjugate region of the first flow path comprises a mobilizable conjugate complex including a first binding partner conjugated to a detectable entity, wherein the first binding partner is capable of specifically binding to a target analyte. The detectable entity can be an enzyme, a metal particle (e.g. metal nanoparticle or metal nanoshell), or a metal particle conjugated to an enzyme. In one embodiment, the mobilizable conjugate complex is an antibody-enzyme conjugate. In another embodiment, the mobilizable conjugate complex is an antibody-nanoparticle conjugate. In yet another embodiment, the mobilizable conjugate complex is an antibody-enzyme-nanoparticle conjugate.

In still other embodiments of the invention, the second flow path of the analyte detection system comprises a substrate region, wherein the substrate region comprises a substrate entity capable of interacting with the detectable entity of the mobilizable conjugate complex to produce a detectable signal. In another embodiment, the substrate entity is capable of interacting with the detectable entity of the mobilizable conjugate complex to amplify the signal from the detectable entity.

In another embodiment of the invention, the capture region of the first flow path comprises a test region and a control region. The test region can comprise an immobilized second binding partner capable of specifically binding to a target analyte. The control region can comprise an immobilized control binding partner. In one embodiment, the control binding partner can bind to unreacted mobilizable conjugate complex. In another embodiment, the control binding partner can bind to an artificial component supplied to the sample.

In some embodiments, the analyte detection system is positioned in an enclosed housing. The housing can comprise one or more vents to facilitate fluid movement through the first and second flow paths.

The present invention also provides a kit comprising an analyte detection system of the invention and instructions for using the system to detect a target analyte in a test sample. The kit can further comprise means for collecting samples and buffers for extracting samples from solid substances.

The present invention includes a method of detecting a target analyte in a test sample. In one embodiment, the method comprises contacting the test sample to the sample loading region of an analyte detection system of the invention and detecting the presence or absence of the target analyte at the capture region of the system. The test sample can be a biological sample isolated from a human or animal subject.

DETAILED DESCRIPTION OF THE INVENTION

Figure 1:
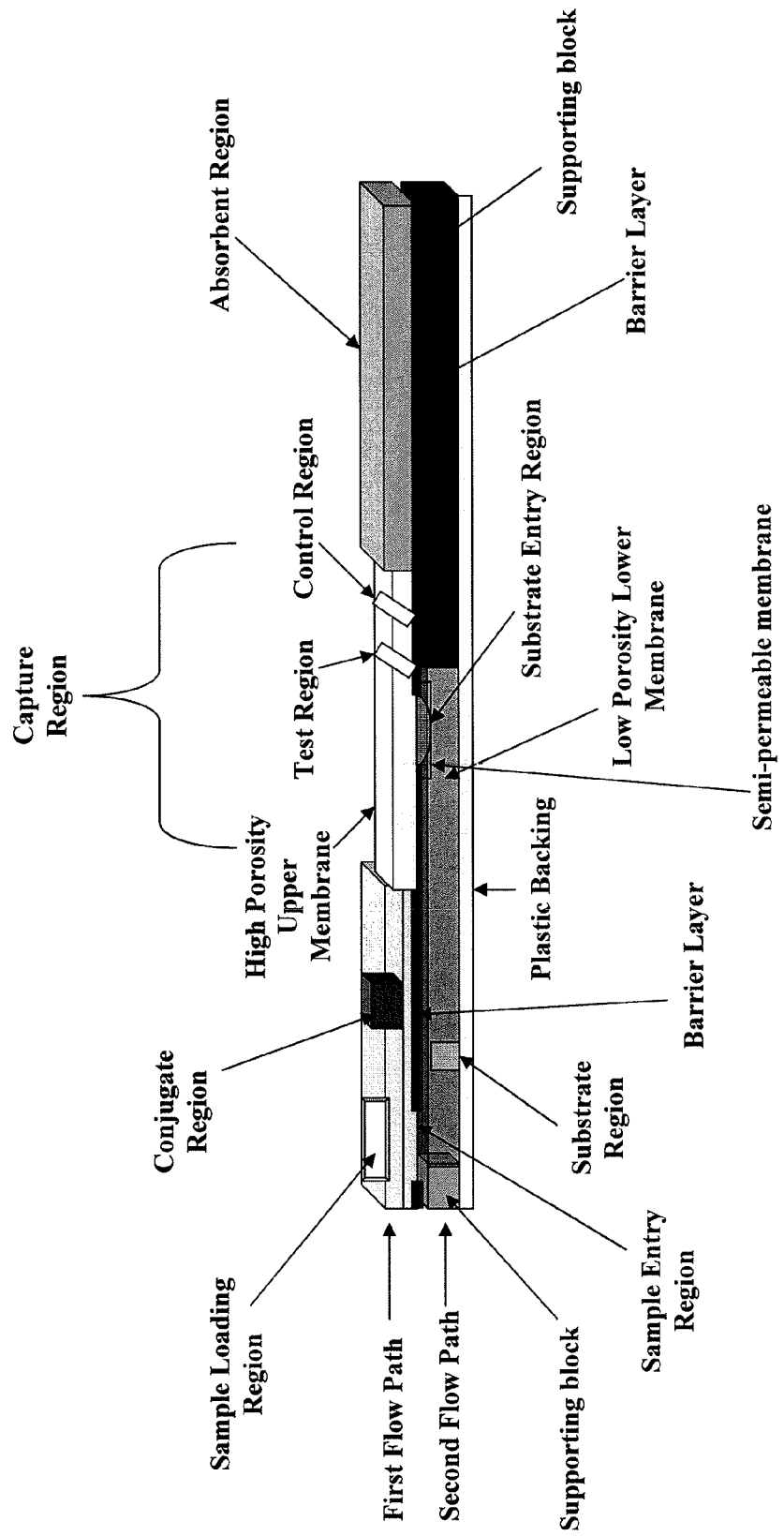
FIG. 1 depicts a perspective view of one embodiment of the analyte detection system of the present invention. In this embodiment, the system comprises a first flow path and a second flow path located in separate, parallel planes. The two flow paths are in fluid communication at the sample entry region and substrate entry region, but are otherwise separated by a water impervious barrier layer. The substrate entry region comprises a semi-permeable membrane that allows substrate reagent solubilized in the second flow path to enter the first flow path without allowing labeled conjugate present in the first flow path to enter the second flow path. Liquid sample deposited in the sample loading region will flow down the first flow path to the conjugate region as well as enter the second flow path through the sample entry region. The flow of sample in the first flow path is faster than the flow of the sample in the second flow path due to a membrane of higher porosity located in the first flow path. Consequently, sample that has interacted with the labeled conjugate in the conjugate region will reach the test region before the substrate reagent solubilized by the portion of the liquid sample that entered the second flow path. An absorbent region is located downstream of the capture region to draw fluid through the system and further facilitate removal of free (e.g. unbound) conjugate from the capture region.

The present invention is based in part on the discovery that two parallel sample flow paths located in different planes can be employed in a lateral flow assay device to deliver reagents sequentially to the capture region of the device allowing for amplification of the detection signal. Accordingly, the present invention provides a sensitive, one-step analyte detection system for the detection of a range of analytes in test samples.

In one embodiment, the analyte detection system comprises a first flow path and a second flow path, wherein the first flow path includes a sample loading region, a conjugate region and a capture region, wherein the second flow path includes a sample entry region, a substrate region and a substrate entry region, wherein the first flow path and the second flow path are in different planes and connected through the sample entry region, and wherein the substrate entry region is in fluid communication with the first flow path.

The first and second flow paths can be separated by one or more barrier layers. In such embodiments, the first and second flow paths are in fluid communication through the sample entry region and the substrate entry region. As used herein, "fluid communication" refers to the ability of a liquid to flow or travel between two materials or surfaces. Fluid communication can be established between two porous materials or between a porous material and a non-porous material. In the latter situation, the non-porous material can form a channel or conduit by which fluid can flow by capillary action to establish fluid communication between the non-porous material and the porous material. The barrier layer can be a water impervious material including, but not limited to, plastic, silica plate, metal plate, or a laminated or coated material.

In some embodiments, the substrate entry region comprises a semi-permeable membrane by which fluid communication is established between the first and second flow paths. As used herein, the term "semi-permeable" refers to a material that allows some molecules to pass through it, but not others. The porosity of the semi-permeable membrane can be selected such that the substrate entity, which is dissolved in the liquid flowing through the second flow path, is allowed to enter the first flow path, but mobilizable conjugate from the first flow path cannot enter the second flow path. The particular porosity of the semi-permeable membrane can be chosen by one of ordinary skill in the art based on the relative molecular sizes of the substrate entity and the mobilizable conjugate. The semi-permeable membrane can be made from a variety of materials including, but not limited to, cellulose acetates, nitrates, and esters (CA, CN, and CE), polysulfone (PS), polyether sulfone (PES), polyacrilonitrile (PAN), nitrocellulose, acrylics, polyamide, polyimide, polyethylene and polypropylene (PE and PP), polytetrafluoroethylene (PTFE), polyvinylidine fluoride (PVDF), polyvinylchloride (PVC), phospholipid bilayers, silicone, and clay materials.

In other embodiments, the substrate entry region contains an air gap that separates the first flow path from the second flow path. Fluid flowing through the second flow path can fill the air gap and establish fluid communication between the first and second flow paths. In another embodiment, the substrate entry region comprises an air gap and a material that expands upon exposure to fluid, wherein the air gap separates the first flow path and the second flow path. The air gap can be eliminated by expansion of the material in the substrate entry region upon contact with fluid from the second flow path thereby establishing fluid communication between the first and second flow paths.

In another aspect of the invention, the first flow path and second flow path are located in separate, parallel planes. In one embodiment, the first flow path is positioned above the second flow path. For instance, the first flow path is located in a top plane whereas the second flow path is located in a bottom plane. In another embodiment, the top plane can be connected to the bottom plane through an opening or port at the sample entry region and/or the substrate entry region. In another embodiment, the top plane is in fluid communication with the bottom plane through the sample entry region. In yet another embodiment, the top plane is in fluid communication with the bottom plane through the substrate entry region. In still another embodiment, the top plane is in fluid communication with the bottom plane through the sample entry region and the substrate entry region.

The first flow path and second flow path can comprise a porous material. A "porous" material refers to a material containing a plurality of interstices or pores through which liquid easily flows. The porous material can be made from natural or synthetic substances. Suitable porous materials for use in the detection system of the present invention include, but are not limited to, nitrocellulosic material, acrylic material, PVDF, polyethylene material (e.g. Porex®), nylon, cellulose acetate, polyester material, PES material, or polysulfone material. Other appropriate porous materials that can be used in the detection systems of the invention are known to those skilled in the art. In one embodiment, the first flow path provides a faster flow through than the second flow path. In another embodiment, the first flow path comprises a first porous material and the second flow path comprises a second porous material, wherein the first porous material has a higher porosity than the second porous material.

In some embodiments, the wicking rates of the first and second flow path can be manipulated to alter the timing of delivery of reagents to a capture region. Wicking rates can be varied by using materials with different porosity or hydrophilicity or using materials containing detergents. For instance, in one embodiment, different wicking rates can be obtained by creating materials with different gradients of porosity or hydrophilicity similar to the manner in which gradient SDS-PAGE gels are created. The porosity gradients may be varied between the first and second porous materials such that the first porous material provides a faster flow through than the second porous material. Methods are known to those skilled in the art by which one may create flat sheet membranes with controlled pore size and pore density. For example, Sirijamkul and others have described the manufacture of track-edge membranes with controlled gradients of pore size and density along the length of the membrane (Journal of Membrane Science, Vol. 296:185-194, 2007). Ceramic membranes with gradient ceramic elements are also known to those skilled in the art (Sui and Huang, Separation and Purification Technology, Vol. 32: 73-79, 2003). In another embodiment, wicking rates of the first and second flow path can be manipulated by using porous material with different pore sizes, pore volumes, and thickness. Decreases in pore size and pore volume and increases in thickness of the material correlate with slower flow rates. Thus, in some embodiments, the second porous material has a smaller pore size and/or less pore volume than the first porous material. In other embodiments, the second porous material is thicker than the first porous material.

In some embodiments of the invention, the first flow path comprises a sample loading region, a conjugate region, and a capture region. The sample loading region can be positioned upstream of the conjugate region, which in turn is positioned upstream of the capture region. As used herein, "upstream" refers to the direction of fluid flow away from the end of the detection system and toward the site of sample application. "Downstream" refers to the direction of fluid flow toward the end of the detection system and away from the site of sample application. Preferably, the sample loading region is in fluid communication with the conjugate region and the conjugate region is in fluid communication with the capture region.

In another embodiment, the first flow path further comprises an absorbent region positioned downstream of the capture region. See, e.g., FIG. 1. The absorbent region can be in fluid communication with the capture region and can be constructed from cellulose materials or the like. The absorbent region can function to facilitate the movement of fluids through both the first and second flow paths of the detection system and to remove excess fluid from other components of the system, such as the conjugate region and capture region. The absorbent region can pull away unreacted (e.g. uncaptured) conjugate, thus preventing an undesirable background noise in the test and control regions.

The sample loading region of the first flow path provides an entry point for liquid sample to be applied to the detection system. As discussed in more detail below, liquid sample applied to the sample loading region can enter the first flow path as well as the second flow path via the sample entry region. In some embodiments, the sample loading region comprises a sample reagent selected from the group consisting of blocking agents, neutralizing agents, buffers, detergents, antimicrobials, and a combination thereof. One or more of the sample reagents may be dried into a pad positioned in the sample loading region. The pad can be manufactured from one of several materials, including but not limited to, polyester, polyacrylic, other polymeric materials, or glass fiber.

In one embodiment, the sample loading region comprises a blocking agent. A "blocking agent" is an agent that prevents the non-specific association of proteins present in the sample with the mobilizable conjugate complex, the immobilized second binding partner, and/or target analyte. Blocking agents are typically proteins themselves and can include, but are not limited to, bovine serum albumin, casein, gelatin, ovalbumin, gamma-globulins, and IgG from non-immunized animals. In another embodiment, the sample loading region comprises a neutralizing agent. A "neutralizing agent" is an agent that reduces the chemical reactivity of at least one interfering species. An interfering species can be a biological molecule or other compound present in a sample that exhibits a non-specific binding affinity to the detectable entity in the mobilizable conjugate complex. Non-limiting examples of neutralizing agents include alkylating agents, such as iodoacetamide, iodoacetate, N-ethylmaleimide, PEG-maleimide, ethlymethanesulfonate, 4-vinylpyridine, nitrogen mustards, nitrosourea compounds, dacarbazine, and temozolomide. Neutralizing agents are described in detail in co-pending U.S. Provisional Application No. 61/079,777, filed Jul. 10, 2008, which is herein incorporated by reference in its entirety.

The sample loading region can comprise other various sample reagents including, but not limited to, buffers for maintaining the pH of the sample, detergents to enhance fluid flow, accelerants for enhancing the rate of immunoreactions, and antimicrobials to prevent biological contamination. Non-limiting examples of suitable buffers include Tris, Hepes, imidazole, phosphate and other standard buffers typically used in lateral flow assays. Suitable detergents that may be used include, but are not limited to, Tween-20, Triton X-100, saponin, zwittergents based on sulfobetaines, CHAPS, octyl glucosides, and lauryl sulfates. Suitable accelerants that may be incorporated into the sample loading region include, but are not limited to, polyethylene glycols, polyvinyl alcohols, and polyvinylpyrrolidones. Exemplary antimicrobials that may be incorporated into the sample loading region include sodium azide, thimerosal, Proclins, antibiotics (e.g. Aminoglycosides, Ansamycins, Carbacephem, Carbapenems, Cephalosporins, Macrolides, Monobactams, Penicillins, Quinolones, Sulfonamides, and Tetracyclines), antivirals (e.g. amantadine, rimantadine, pleconaril, acyclovir, zanamivir, and oseltamivir), antifungals (e.g. Natamycin, Rimocidin, Filipin, Nystatin, Amphotericin B, Candicin, Imidazoles, Triazoles, Allylamines, and Echinocandins), and antiparasitics (e.g. Mebendazole, Pyrantel pamoate, Thiabendazole, Diethycarbazine, Niclosamide, Praziquantel, Rifampin, Amphotericin B, and Melarsoprol). One of ordinary skill in the art can select other appropriate antimicrobials; buffers, accelerants, and detergents based on the particular sample type to be screened and the particular target analyte to be assayed without undue experimentation.

In another aspect of the invention, the first flow path comprises a conjugate region downstream of the sample loading region. In one embodiment, the conjugate region comprises a mobilizable conjugate complex. The mobilizable conjugate complex includes a first binding partner conjugated to a detectable entity. The first binding partner can be any entity that is capable of specifically binding to a target analyte. In some embodiments, the first binding partner is a biological macromolecule, including but not limited to an antibody or a region thereof (e.g., Fv, single chain, CDR, antibody expressed in phage display, etc.), a receptor, a ligand, a polynucleotide, an aptamer, a polypeptide, a polysaccharide, a lipopolysaccharide, a glycopeptide, a lipoprotein, or a nucleoprotein. In one embodiment, the first binding partner is an antibody. The conjugate region can comprise one or more excipients to stabilize the mobilizable conjugate complex. Such excipients will depend on the type of binding partner and detectable entity that comprise the mobilizable complex, but can include albumins, caseins, gelatin, polymeric stabilizers such as polyvinylpyrrolidone or polyvinyl alcohol, or sugars like sucrose and trehalose.

As used herein, "detectable entity" is an entity that is capable of producing a detectable signal under a particular set of conditions. In one embodiment, the detectable entity is an entity that exhibits wavelength selective absorption in the ultra-violet, visible, or near infrared electromagnetic spectrum and scatters incident radiation. For instance, the detectable entity can be a metallic nanoparticle or metallic nanoshell. Various types of metallic nanoparticles that can be coupled to the first binding partner include, but are not limited to, gold nanoparticles, silver nanoparticles, copper nanoparticles, platinum nanoparticles, cadmium nanoparticles, composite nanoparticles (e.g. silver and gold or copper and silver), and gold hollow spheres. In some embodiments, the detectable entity is a gold nanoparticle. Additionally, metal nanoshells as described in U.S. Pat. No. 6,699,724, which is herein incorporated by reference in its entirety, can also be used as the detectable entity. Metal nanoshells are particles comprised of a dielectric core and a metallic coating that have a defined core radius to shell thickness ratio. The core can be comprised of a variety of materials including silicon dioxide, gold sulfide, titanium dioxide, and polystyrene. Suitable metals for the shell include gold, silver, copper, platinum, palladium, lead, and iron. Gold-coated silica nanoshells or silica-coated gold shells are preferred in some embodiments.

In another embodiment, the detectable entity is an entity that converts a substrate into a signaling entity, e.g., colored, fluorescent, or chemiluminescent product. For instance, the detectable entity can be an enzyme. Non-limiting examples of enzymes that are suitable for conjugation to the first binding partner include alkaline phosphatase, horseradish peroxidase, beta-galactosidase, beta-lactamase, galactose oxidase, lactoperoxidase, luciferase, myeloperoxidase, and amylase. In another embodiment, the detectable entity is a metallic nanoparticle conjugated to an enzyme. Other molecules, such as fluorescent molecules (e.g. fluorescein, Texas-Red, green fluorescent protein, yellow fluorescent protein, cyan fluorescent protein, Alexa dye molecules, etc.), that are known to those skilled in the art can be used as detectable entities in the mobilizable conjugate complexes of the invention. In one embodiment, the mobilizable conjugate complex is an antibody-enzyme conjugate. In another embodiment, the mobilizable conjugate complex is an antibody-nanoparticle conjugate. In another embodiment, the mobilizable conjugate complex is an antibody-enzyme-nanoparticle conjugate. The enzyme in such conjugate complexes can be alkaline phosphatase, horse radish peroxidase, or β-galactosidase.

Methods of conjugating a detectable entity (e.g. metallic nanoparticles, metallic nanoshells, and enzymes) to a binding partner are well known in the art. One such method for coupling a metallic nanoparticle or metallic nanoshell to a binding partner is by passive adsorption. This method involves adjusting the pH of the metal colloid solution to a pH at which the protein or other binding partner to be labeled has a positive charge, mixing the metal colloid solution with the binding partner solution, and centrifuging the resultant mixture. The labeled binding partner (e.g. protein) is then obtained by removing the supernatant and resuspending the precipitate. One example of a method for conjugating an enzyme to a binding partner, such as an antibody, is described in U.S. Pat. No. 5,164,311, which is herein incorporated by reference in its entirety. The method entails introducing sulfhydryl groups into the antibody and maleimide groups into the enzyme and mixing the two modified groups in a particular ratio. Other methods of conjugating macromolecules to detectable entities are known to the skilled artisan, who can select the proper method based on the type of desired detectable entity to be used and the type of macromolecule to be labeled. In some embodiments, the binding partner can be coupled to the detectable entity indirectly through a larger carrier molecule or protein. Such indirect coupling is particularly useful when the binding reagent is small, such as hormones, drugs, and other small molecules less than 10 kD. Preferably, the carrier protein is not capable of specific interaction with the target analyte. In other embodiments, gold or other metallic nanoparticles can be conjugated to an antibody-enzyme complex to form an antibody-nanoparticle-enzyme conjugate using the procedures mentioned above. Such procedures are widely known to those skilled in the art. In some embodiments, the first binding partner is coupled to the detectable entity to form the mobilizable conjugate complex prior to deposition of the complex in the conjugate region.

In another aspect of the invention, the first flow path comprises a capture region downstream of the conjugate region. In one embodiment, the capture region comprises a test region. The test region can comprise an immobilized second binding partner capable of specifically binding to a target analyte. The second binding partner can be a biological macromolecule, such as an antibody or a region thereof (e.g., Fv, single chain, CDR, antibody expressed in phage display, etc.), a receptor, a ligand, a polynucleotide, an aptamer, a polypeptide, a polysaccharide, a lipopolysaccharide, a glycopeptide, a lipoprotein, or a nucleoprotein. In some embodiments whole cells, bacteria, or viruses can be immobilized to serve as the second binding partners. The second binding partner can be the same type of molecule as the first binding partner in the mobilizable conjugate complex, but preferably interacts with the target analyte at a location distinct from that as the first binding partner. By way of example, the first binding partner and the second binding partner can both be antibodies that recognize a target analyte, but the epitope to which the first binding partner binds the target analyte is separate from the epitope to which the second binding partner binds the target analyte.

In another embodiment, the capture region further comprises a control region. The control region can operate as a positive control for the detection system. For instance, a detectable signal in the control region may indicate that the liquid sample applied to the detection system has reached the capture region of the system (e.g. the fluidics of the first flow path are functioning properly). This function of the control region helps to eliminate false negatives due to improper flow of the sample through the detection system. In some embodiments, the control region comprises an immobilized control binding partner. In one embodiment, the control binding partner is capable of specifically binding to the unreacted mobilizable conjugate complex (e.g. the first binding partner or detectable entity). By way of example, the control binding partner can be an antibody that specifically binds to the first binding partner or detectable entity. Preferably, the detection signal is the same for both the test region and control region. For instance, where the mobilizable conjugate comprises an antibody coupled to alkaline phosphatase, the control binding partner can be an anti-alkaline phosphatase antibody that would capture unreacted mobilizable conjugate flowing downstream of the test region. The bound mobilizable conjugate at the control region would be detected by subsequent delivery of the substrate for alkaline phosphatase (e.g. BCIP/NBT).

In another embodiment, the control binding partner is capable of specifically binding to an artificial component (e.g. conjugate) that has been added to the sample. The artificially added conjugate can be supplied to the sample prior to sample application to the detection system or it may be dried into a sample pad located in the sample entry region of the system. For instance, biotin coupled to a detectable entity (e.g. biotin conjugate) can be supplied to the sample. In this case, the control binding partner can be streptavidin, which would bind the artificially added biotin conjugate. In preferred embodiments, the detectable entity coupled to the artificially added substance is the same as the detectable entity in the mobilizable conjugate complex.

In still another embodiment, the capture region can comprise a second control region (e.g. an independent bottom plane control region). This second control region can serve as a positive control for proper fluid flow through the second flow path of the detection system. As discussed in more detail below, the second flow path comprises a substrate or amplifying reagent to visualize or enhance the signal from the detectable entity of the mobilizable conjugate complex. Thus, the second control region can function to eliminate false negatives due to failure of the substrate or amplifying reagent to be delivered to the capture region of the detection system. Preferably, the second control region is located downstream of the test region and first control region. See, e.g., FIG. 4. In some embodiments, the second control region can comprise a pH indicator dye. The type of indicator dye will depend on the nature and required solvent for the substrate or amplifying reagent located in the second flow path. For example, a basic pH indicator dye may be used where the solubilized substrate produces an alkaline solution. In other embodiments, the second control region can comprise an immobilized enzyme, which can convert the solubilized substrate into a colored or fluorescent product.

In some embodiments, the second binding partner is immobilized to a porous surface in the test region and the control binding partner is immobilized to a porous surface in the control region. The binding partners can be immobilized on a porous surface by a variety of procedures. The binding partners (e.g. second binding partner and control binding partner) can be striped, deposited, or printed on the porous surface followed by drying of the surface to facilitate immobilization. Immobilization of the binding partners can take place through adsorption or covalent bonding. Depending on the nature of the porous surface (e.g. type of porous material), methods of derivatization to facilitate the formation of covalent bonds between the porous surface and the binding partner can be used. Methods of derivatization can include treating the porous surface with a compound, such as glutaraldehyde or carbodiimide and applying the binding partner. Other physical, chemical, or biological methods of immobilizing a macromolecule or other substance either directly or indirectly to a porous material are known in the art and can be used to immobilize the second or control binding partner to the porous surface in the capture region of the detection system. In some embodiments, the porous surface in the test region and control regions may be treated with a blocking agent, such as bovine serum albumin or other blocking agent as described herein.

In yet another aspect of the invention, the second flow path comprises a sample entry region, a substrate region, and a substrate entry region. The sample entry region can be positioned upstream of the substrate region, which in turn is positioned upstream of the substrate entry region. See, e.g., FIG. 1. The sample entry region can be in fluid communication with the first flow path. In some embodiments, the sample entry region is directly connected (e.g. no intervening material) to the first flow path. The substrate entry region can also be in fluid communication with the first flow path. In some embodiments, fluid communication between the substrate entry region and the first flow path is established through a semi-permeable membrane or an air gap that fills upon liquid absorption. Preferably, fluid from the second flow path re-enters the first flow path upstream of the test region through the substrate entry region.

In one embodiment, the second flow path comprises a substrate region downstream of the sample entry region. The substrate region can contain a pad in which one or more reagents (e.g. enzyme substrates, amplifying reagents, polymers, etc.) are dried. In some embodiments of the invention, the conjugate region comprises a mobilizable conjugate complex including a first binding partner conjugated with a detectable entity and the substrate region comprises a substrate entity capable of interacting with the detectable entity to produce a detectable signal. By way of illustration, if the mobilizable conjugate complex comprises an enzyme as the detectable entity, the substrate region can comprise a substrate for that enzyme wherein a colored, fluorescent, or chemiluminescent substance is produced from the substrate after reaction with the enzyme. The specific substrate will depend upon the type of enzyme used as the detectable entity and the type of signal desired (e.g. color change or fluorescent signal). Some examples of suitable substrates include, but are not limited to, 2,2'-Azino-bis-(3-ethylbenziazoline-6-sulfonic acid) (ABTS), 3-Amino-9-ethylcarbazole (AEC), 5-bromo-4-chloro-3-indolylphosphate/nitroblue tetrazolium chloride (BCIP/NBT), 5-bromo-4-chloro-3-indolylphosphate/tetranitroblue tetrazolium (BCIP/TNBT), Lumiphos®, 3,3'-Diaminobenzidine (DAB), 3,3',5,5'-Tetramethylbenzidine (TMB), 5-bromo-4-chloro-3-indolyl-beta-D-galactopyranoside (X-Gal), phosphastes of indoxyls substituted at various positions in combination with a variety of tetrazolium dyes, naphthol phosphates in combination with Fast dyes, 4-CN, cobalt-DAB, and Gold-DAB. Various chromogenic, fluorogenic, and chemiluminescent substrates are commercially available for standard enzymes, such as alkaline phosphatase and horseradish peroxidase. Such commercially available enzyme substrates can be used in the detection system of the invention.

In other embodiments of the invention, the conjugate region comprises a mobilizable conjugate complex including a first binding partner conjugated with a detectable entity and the substrate region comprises a substrate entity capable of interacting with the detectable entity to amplify the signal from the detectable entity. For instance, in one embodiment, the detectable entity is a gold nanoparticle and the substrate entity is silver nitrate. In another embodiment, the detectable entity is a metallic nanoparticle and the substrate entity is 3,3',5,5'-Tetramethylbenzidine (TMB) or an indigo-containing product. The substrate region may comprise one or more amplifying reagents that intensify the signal from the detectable entity (e.g. metal nanoparticles or metal nanoshells). Such amplifying reagents include, but are not limited to, silver nitrate, silver acetate, silver citrate, osmium tetroxide, diaminobenzidine, tetrazolium dyes, peroxidase reaction product of 3,3',5,5'-Tetramethylbenzidine (TMB), alkaline phosphatase reaction product of BCIP or any other indigo-containing product (e.g. 3-IP or any of the other substituted indoxyl phosphates). In another embodiment, the substrate entity produces a product that enhances the color of metallic nanoparticles. The product may be formed enzymatically. For instance, in one embodiment, the detectable entity is a metallic nanoparticle conjugated to an enzyme and the substrate entity is a substrate of the enzyme. In some embodiments, the detectable entity is a gold nanoparticle-enzyme conjugate and the substrate entity is 3,3',5,5'-Tetramethylbenzidine (TMB) or an indigo-containing product (e.g. BCIP or 3-IP).

The substrate region can comprise one or more additional reagents that act to slow the flow of fluid through the second flow path. In one embodiment, the substrate region comprises one or more slowly dissolving polymers (e.g. dissolution retardants), such as polyvinylpyrrolidone, polyvinyl alcohol, polyethylene glycol, ethylcellulose, hydroxypropylmethylcellulose, Eudragit® and equivalent polymethacrylate products, hydroxypropylethylcellulose and hydroxypropylcellulose, or various guar gums, to retard the dissolution of dried substrate or amplifying reagent present in the substrate region, thus prolonging the delivery of the substrate or amplifying reagent to the capture region of the detection system. In some embodiments, higher molecular weight polyvinylpyrrolidones are preferred. In still another embodiment, the substrate region is gelled with calcium-alginate and is fluidized with EGTA contained in a sample conditioning region.

In yet another aspect of the invention, the detection system may further comprise one or more supporting blocks. The supporting blocks may be positioned between the first flow path and the second flow path. In one embodiment, the supporting blocks are positioned underneath the first flow path (e.g. top plane) and adjacent to the second flow path (e.g. bottom plane). Such supporting blocks can function to keep the top and bottom planes separated from each other and lend support to the structure of the detection system. In another embodiment, the detection system may further comprise a plastic backing that extends along the bottom surface of the second flow path (e.g. bottom plane).

In some embodiments of the invention, the analyte detection system is positioned in an enclosed housing. Preferably the housing is constructed from a type of plastic material. The housing should not interfere with the flow paths of the sample within or between the first and second flow paths or impair sample application or the reading of the results. In one embodiment, the housing comprises a sample port positioned over the sample loading region. In another embodiment, the housing comprises a test window positioned over the capture region. The housing can include one or more vents to facilitate fluid movement through the first flow path or second flow path of the detection system. In some embodiments, the vents can be located in the housing forming the side walls of the device. In other embodiments, the vents can be positioned in the housing forming the top cover of the device. In another embodiment, the housing can contain an absorbent pill to keep the porous surfaces in the detection system from absorbing moisture.

One embodiment of the analyte detection system of the invention is illustrated in FIG. 1. In this embodiment, the detection system comprises a first flow path and a second flow path, wherein the first flow path includes a sample loading region, a conjugate region, a capture region, and an absorbent region, and wherein the second flow path includes a sample entry region, a substrate region and a substrate entry region. The first and second flow paths are located in two different planes and are in fluid communication through the sample entry region and the substrate entry region.

A liquid sample placed in the sample loading region splits into two flow paths: the first flow path located in the top plane of the detection system and the second flow path located in the bottom plane of the detection system. The sample flowing through the first flow path will pass through the conjugate region where it will solubilize the dried mobilizable conjugate complex. If the target analyte is present in the sample, the mobilizable conjugate complex will bind to the target analyte and continue to flow into the capture region. The immobilized second binding partner present in the test region of the capture region will bind to and capture the target analyte-mobilizable conjugate complex. Fluid containing unreacted mobilizable conjugate (e.g. not bound to the target analyte) will pass through the test region and into the control region where the immobilized control binding partner will capture some of the mobilizable conjugate. The remaining sample will continue to flow into the absorbent region at the end of the detection system.

The sample that has entered the second flow path via the sample entry region will flow into the substrate region where it will dissolve lyophilized substrate or amplifying reagent. The sample containing the dissolved reagent will continue to flow through the second flow path to the substrate entry region where it will rejoin the first flow path upstream of the test region. The fluid flow through the second flow path will be slower than that through the first flow path due to the presence of a lower porosity membrane in the second flow path. Additionally, any polymers (e.g. dissolution retardants) that are present in the substrate region can cause the substrate or amplifying reagent to dissolve slowly, which contributes to the slower migration of the substrate through the second flow path. This configuration allows for the substrate or amplifying reagent to be delivered to the capture region (e.g. test and control regions) following capture of the mobilizable conjugate complex. The substrate or amplifying reagent will interact with any captured mobilizable conjugate complex in the test and/or control regions to produce or amplify a detection signal.

Figure 2:
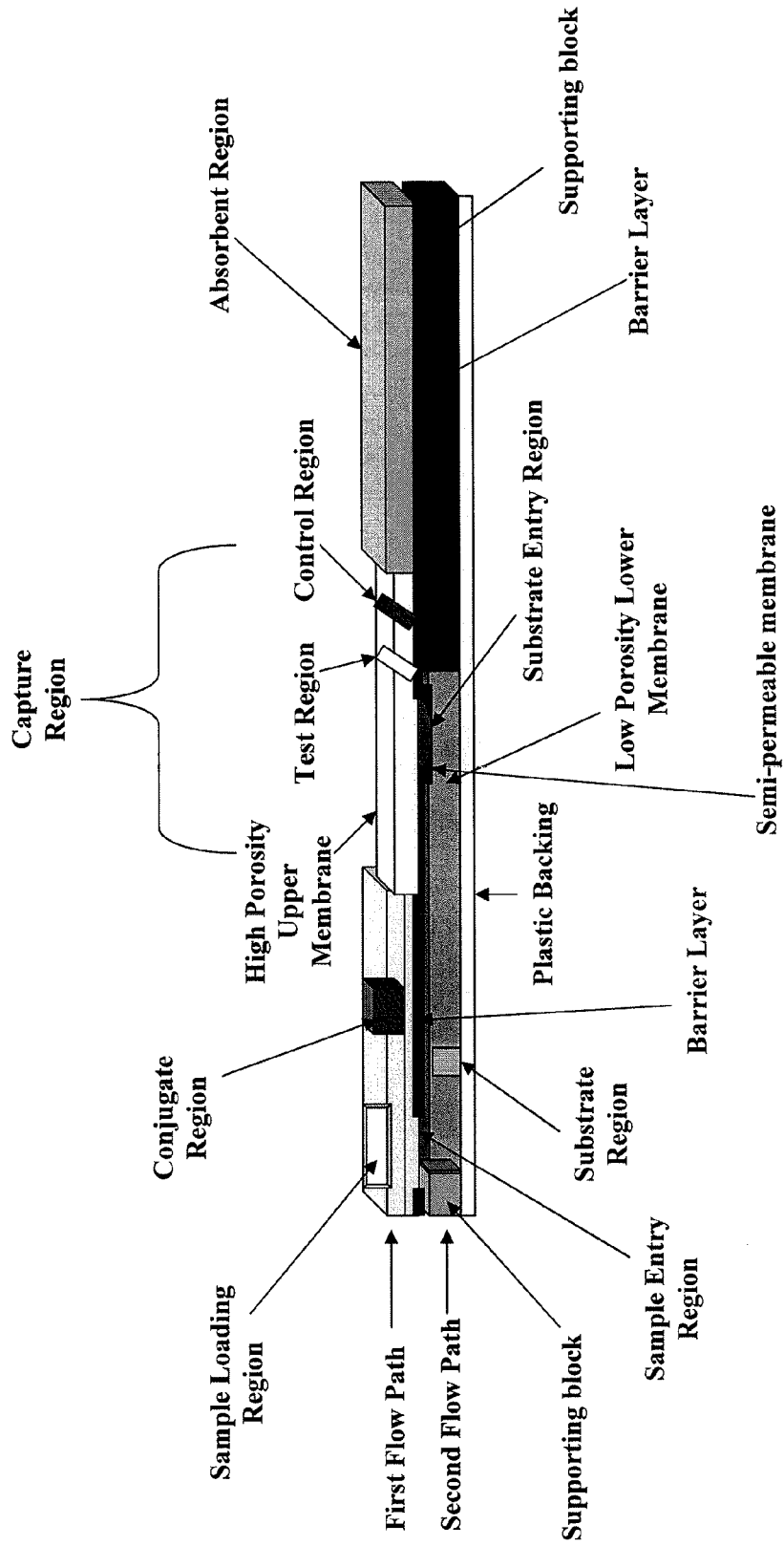
FIG. 2 illustrates the appearance of the analyte detection system shown in FIG. 1 after testing with a negative sample. The color of the control region is changed indicating that the sample has reached the capture region. The test region remains colorless because no analyte is present in the sample to be captured by the immobilized binding partner present in the test region.

FIG. 2 illustrates the appearance of an embodiment of the detection system after application of a sample that does not contain the target analyte (e.g. negative sample). Because no target analyte is present in the sample, the mobilizable conjugate complex is not captured by the immobilized second binding partner in the test region and the unreacted mobilizable conjugate complex passes into the control region. The control binding partner immobilized in the control region will bind to and capture the unreacted mobilizable conjugate complex. Substrate or amplifying reagent delivered from the second flow path will interact with the detectable entity in the captured mobilizable conjugate complex in the control region to produce or enhance a detectable signal. Thus, a detection signal (e.g. color change) will be evident in the control region indicating the successful fluid flow through the detection system. However, no signal will be present in the test region indicating that the sample is negative for the target analyte.

Figure 3:
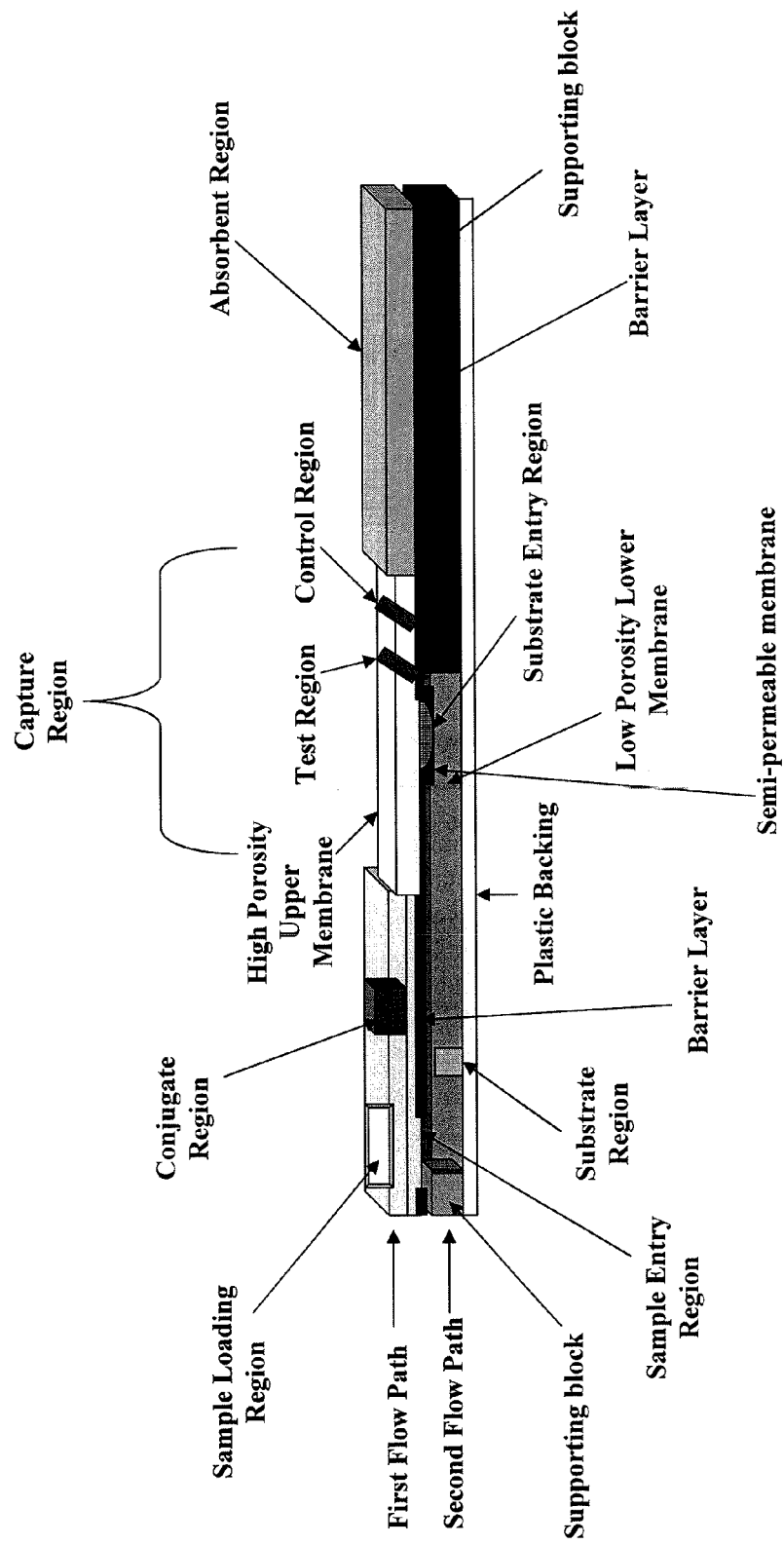
FIG. 3 illustrates the appearance of the analyte detection system shown in FIG. 1 after testing with a positive sample. The color of both the control and test regions is changed, respectively indicating the successful fluid flow through the device and the presence of analyte in the sample.

FIG. 3 illustrates the appearance of an embodiment of the detection system after application of a sample containing the target analyte (e.g. positive sample). After the mobilizable conjugate complex is solubilized by the sample passing through the conjugate region, the target analyte will bind to the first binding partner found in the mobilizable conjugate complex. The target analyte-mobilizable conjugate complex will subsequently bind to the immobilized second binding partner present in the test region of the capture region of the detection system. Any of the mobilizable conjugate that is not bound to target analyte will flow through the test region and a portion of the mobilizable conjugate will bind to the control binding partner immobilized in the control region. Substrate or amplifying reagent delivered by the second flow path will interact with the detectable entity in the captured mobilizable conjugate complex in both the test region and control region. A detectable signal will be evident in both the control and test regions indicating respectively successful performance of the test (e.g. proper fluid flow through the system) and the presence of target analyte in the sample.

Figure 4:
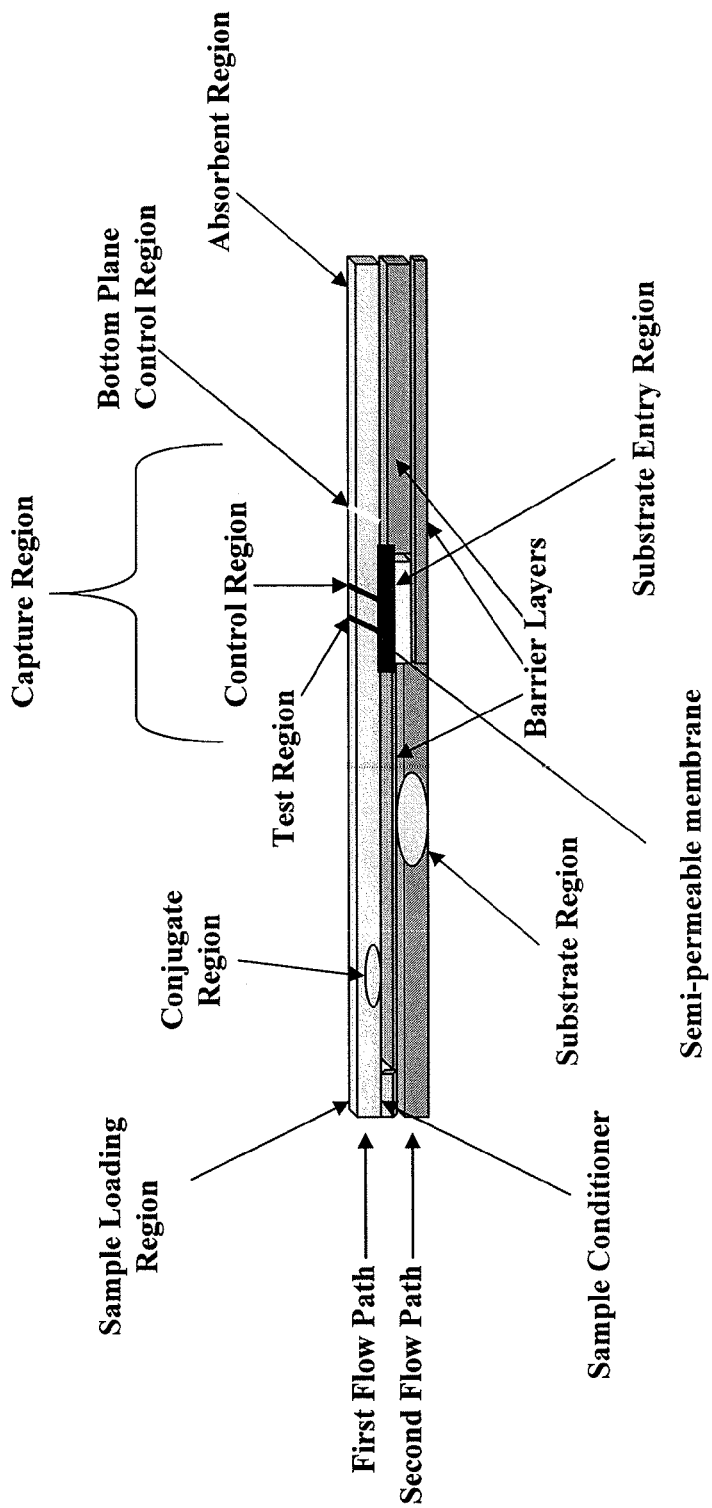
FIG. 4 depicts another embodiment of the analyte detection system of the invention. In this embodiment, the detection system is in a dipstick format that allows sample deposited on the sample loading region to split into two flow paths: a first flow path and a second flow path. The first flow path comprises a conjugate region and a capture region, while the second flow path comprises a substrate region and a substrate entry region. The two flow paths are separated by a water impervious barrier layer and are in fluid communication only at the sample loading region and substrate entry region. In some embodiments, the substrate entry region comprises a semi-permeable membrane. The detection system can contain a sample conditioning region located between the two flow paths at the sample loading region. The system can also contain a second control region (e.g. bottom plane control region), which indicates successful fluid flow through the second flow path of the system.

In another embodiment of the invention, the components of the analyte detection system may be assembled into a dipstick format as illustrated in FIG. 4. In this format, the detection system comprises a first flow path and a second flow path, wherein the first flow path includes a sample loading region, a conjugate region, a capture region, and an absorbent region, and wherein the second flow path includes a substrate region and a substrate entry region. The first and second flow paths are located in two different planes and separated by one or more water impervious barrier layers. A sample conditioning region may optionally be positioned between the first and second flow paths such that liquid sample applied to the sample loading region would flow into the sample conditioning region and into the second flow path. The first and second flow paths are in fluid communication at the substrate entry region.

The sample conditioning region, if present, can contain one or more reagents for changing the properties of the sample to improve fluid flow through the system or enhance the performance of the assay. Such reagents may alter the pH, salt concentration, or metal ion concentration of the sample or may add or remove inorganic or organic compounds or detergents. The sample conditioning region can contain buffers, neutralizing agents, or blocking agents as described above. In some embodiments, the sample conditioning region can contain an amplification reagent as described herein.

Fluid flow through the dipstick embodiment of the detection system is similar to that in the embodiment shown in FIG. 1. Sample may be applied to the sample loading region in the first flow path. The sample would then flow through the first flow path as well as enter the second flow path through the connection at the most upstream end of the device. Alternatively, the detection system may be "dipped" in sample by inserting the most upstream end of the system (e.g. end where the sample loading region is located) into a test tube or other container containing liquid sample. Sample would then enter both the first and second flow paths simultaneously. However, flow through the second flow path would be slower than the flow in the first flow path due to differences in membrane porosity. Also, the second flow path may optionally contain reagents in the substrate region which would retard the fluid flow. Therefore, sample and reagents (e.g. mobilizable conjugate complex) in the first flow path would reach the capture region prior to sample and reagents (e.g. substrate or amplifying reagents) in the second flow path. In some embodiments, a gating mechanism can be employed by inserting a semi-permeable membrane between the first and the second flow paths at the substrate entry region.

The present invention also includes kits comprising the analyte detection systems of the invention as disclosed herein. In one embodiment, the kit comprises an analyte detection system and instructions for using the system to detect an analyte in a test sample, wherein the detection system comprises a first flow path and a second flow path, said first flow path including a sample loading region, a conjugate region and a capture region, said second flow path including a sample entry region, a substrate region and a substrate entry region, wherein the first flow path and the second flow path are in different planes and connected through the sample entry region, and wherein the substrate entry region is in fluid communication with the first flow path. The kit can further include means for collecting biological samples or extraction buffers for obtaining samples from solid materials, such as soil, food, and biological tissues.

The present invention also encompasses a method of detecting a target analyte in a test sample. In one embodiment, the method comprises contacting the test sample with the sample loading region of a detection system disclosed herein and detecting the presence or absence of the target analyte at the capture region. In another embodiment, the method comprises immersing the most upstream end of a detection system disclosed herein in a test sample and detecting the presence or absence of the target analyte at the capture region.

A test sample can be any type of liquid sample, including biological samples or extracts prepared from environmental or food samples. In a preferred embodiment, the test sample is a biological sample. Biological samples include, but are not limited to, blood, plasma, serum, urine, pleural effusion, sweat, bile, cerebrospinal fluid, fecal material, vaginal fluids, sperm, biopsy tissues, and saliva. The biological sample can be obtained from a human subject or animal subject suspected of having a disease condition, such as cancer, infectious diseases (e.g., viral-, bacterial-, parasitic- or fungal-infections), cardiovascular disease, autoimmune etc. The biological sample can also be obtained from a healthy subject (e.g. human or animal) undergoing a routine medical check-up.

Any type of target analyte can be detected using the methods of the present invention. An "analyte" refers to any substance capable of being bound by a binding partner of the mobilizable conjugate complexes disclosed herein. An analyte encompasses derivatives or metabolites of the compound of interest. In some embodiments, the analytes are associated with infectious diseases in both humans and animals. In other embodiments, the analytes are markers of a particular physiological or pathological condition. A target analyte can be a protein, peptide, nucleic acid, hapten, or chemical.

Detection of the presence or absence of the target analyte in the capture region comprises observing or measuring the signal from the detectable entity of captured mobilizable conjugate complexes. In some embodiments, the signal is a spectral shift (e.g. color change of the capture line and/or conjugate). In other embodiments, the signal is a fluorescent signal. The detection signal corresponding to the presence of any captured mobilizable conjugate complex in the test and/or control regions can be detected visually or by means of an instrument. In one embodiment, the signal is detected by measuring a change in absorbance of the signal. Commercial instruments capable of detecting spectral shifts or changes in fluorescence can be used to measure the detection signal from captured mobilizable conjugate complexes of the detection systems. Such instruments include "strip readers" and are known to those skilled in the art. Detection of a signal in the control region of the analyte detection systems of the invention is indicative of proper fluid flow through the device. Detection of a signal in the test region of the analyte detection systems of the invention is indicative of the presence of target analyte in the test sample (e.g. positive sample). Similarly, absence of a signal in the test region of the analyte detection systems of the invention is indicative of the absence of target analyte in the test sample (e.g. negative sample).

It is understood that the disclosed invention is not limited to the particular methodology, protocols and materials described as these can vary. It is also understood that the terminology used herein is for the purposes of describing particular embodiments only and is not intended to limit the scope of the present invention which will be limited only by the appended claims.

Those skilled in the art will recognize, or be able to ascertain using no more than routine experimentation, many equivalents to the specific embodiments of the invention described herein. Such equivalents are intended to be encompassed by the following claims.

The invention claimed is:

1. An analyte detection system comprising:
a first flow path including a sample loading region, a conjugate region comprising a mobilizable conjugate complex, and a capture region comprising an immobilized binding partner capable of specifically binding to a target analyte, and
a second flow path including a sample entry region, a substrate region comprising a substrate entity, and a substrate entry region, wherein said substrate region is positioned upstream of said substrate entry region,
wherein the first flow path and the second flow path are in different planes and connected through the sample entry region,
wherein the substrate entry region comprises a semi-permeable membrane that establishes fluid communication between the first and second flow paths, and
wherein said semi-permeable membrane has a porosity such that the substrate entity may pass to the first flow path from the second flow path, but mobilizable conjugate complex cannot pass from the first flow path to the second flow path.

2. The detection system of claim 1, wherein the first flow path further comprises an absorbent region downstream of the capture region.

3. The detection system of claim 1, wherein the capture region comprises a test region and a control region, wherein the test region comprises said immobilized binding partner.

4. The detection system of claim 3, wherein the control region comprises an immobilized control binding partner.

5. The detection system of claim 3, wherein the substrate entry region comprising the semi-permeable membrane is positioned such that fluid flow through the second flow path re-enters the first flow path upstream of the test region.

6. The detection system of claim 1, wherein the first flow path and the second flow path are separated by a barrier layer.

7. The detection system of claim 1, wherein the first flow path provides a faster flow through than the second flow path.

8. The detection system of claim 1, wherein the first flow path comprises a first porous material and the second flow path comprises a second porous material, and wherein the first porous material has a higher porosity than the second porous material.

9. The detection system of claim 1, wherein said mobilizable conjugate complex includes a binding partner conjugated to a detectable entity and wherein the binding partner is capable of specifically binding to the target analyte.

10. The detection system of claim 9, wherein the binding partner is an antibody, receptor, ligand, polynucleotide, polypeptide, polysaccharide, aptamer, lipopolysaccharide, lipoprotein or nucleoprotein.

11. The detection system of claim 9, wherein the detectable entity is an enzyme.

12. The detection system of claim 11, wherein the enzyme is selected from the group consisting of alkaline phosphatase, horseradish peroxidase, beta-galactosidase, beta-lactamase, luciferase, myeloperoxidase, and amylase.

13. The detection system of claim 9, wherein the detectable entity is a metallic nanoparticle or metallic nanoshell.

14. The detection system of claim 13, wherein the detectable entity is selected from the group consisting of gold nanoparticles, silver nanoparticles, copper nanoparticles, platinum nanoparticles, cadmium nanoparticles, composite nanoparticles, gold hollow spheres, gold-coated silica nanoshells, and silica-coated gold shells.

15. The detection system of claim 9, wherein the detectable entity is a metallic nanoparticle conjugated to an enzyme.

16. The detection system of claim 9, wherein the substrate entity is capable of interacting with the detectable entity to produce a detectable signal.

17. The detection system of claim 9, wherein the substrate entity is capable of interacting with the detectable entity to amplify the signal from the detectable entity.

18. The detection system of claim 17, wherein the detectable entity is a gold nanoparticle and the substrate entity is silver nitrate, silver acetate, or silver citrate.

19. The detection system of claim 17, wherein the detectable entity is a metallic nanoparticle and the substrate entity is the peroxidase reaction product of 3, 3', 5, 5'-Tetramethylbenzidine (TMB) or an alkaline phosphatase reaction product of 5-bromo-4-chloro-3-indolyl phosphate (BLIP).

20. The detection system of claim 17, wherein the detectable entity is a metallic nanoparticle conjugated to an enzyme and the substrate entity is a substrate of the enzyme.

21. The detection system of claim 20, wherein the detectable entity is a gold nanoparticle-enzyme conjugate and the substrate entity is TMB or BCIP.

22. The detection system of claim 1, wherein said mobilizable conjugate complex is selected from the group consisting of antibody-enzyme conjugate, antibody-nanoparticle conjugate, and antibody-enzyme-nanoparticle conjugate.

23. The detection system of claim 1, wherein the sample loading region comprises a sample reagent selected from the group consisting of blocking agents, neutralizing agents, buffers, detergents, antimicrobials, and a combination thereof.

24. The detection system of claim 1, wherein the system is positioned in an enclosed housing.

25. The detection system of claim 24, wherein the housing comprises a vent to facilitate fluid movement through the first flow path or second flow path.

26. A kit comprising the detection system of claim 1 and instructions for using the system to detect an analyte in a test sample.

27. The detection system of claim 1, wherein the capture region comprises a test region, a first control region, and a second control region, wherein said first control region indicates fluid flow through the first flow path and said second control region indicates fluid flow through the second flow path.

28. The detection system of claim 27, wherein the second control region is located downstream of the test region and the first control region.

29. The detection system of claim 27, wherein the second control region comprises a pH indicator dye or an immobilized enzyme.

30. A method of detecting a target analyte in a test sample comprising contacting the test sample to the detection system of claim 1 and detecting the presence or absence of the target analyte at the capture region.

31. An analyte detection system comprising:
a first flow path including a sample loading region, a conjugate region, and a capture region, and
a second flow path including a sample entry region, a substrate region, and a substrate entry region,
wherein the first flow path and the second flow path are in different planes and connected through the sample entry region,
wherein the substrate entry region comprises a semi-permeable membrane thereby establishing fluid communication with the first flow path, and
wherein the capture region comprises a test region, a first control region, and a second control region, said first control region indicating fluid flow through the first flow path and said second control region indicating fluid flow through the second flow path.

32. The detection system of claim 31, wherein the second control region is located downstream of the test region and the first control region.

33. The detection system of claim 31, wherein the second control region comprises a pH indicator dye or an immobilized enzyme.

* * * * *